(12) United States Patent
Springstead

(10) Patent No.: US 7,060,306 B2
(45) Date of Patent: Jun. 13, 2006

(54) SKIN FORMULATION

(76) Inventor: Patricia R. Springstead, 181 Mount Fair Ave., Brooksville, FL (US) 34601

( * ) Notice: Subject to any disclaimer, the term of this patent is extended or adjusted under 35 U.S.C. 154(b) by 280 days.

(21) Appl. No.: 10/703,427

(22) Filed: Nov. 10, 2003

(65) Prior Publication Data

US 2005/0100524 A1    May 12, 2005

(51) Int. Cl.
*A01N 65/00*    (2006.01)

(52) U.S. Cl. ............... 424/725; 424/736; 424/745; 424/761; 424/766; 424/770; 424/777; 424/539

(58) Field of Classification Search .............. None
See application file for complete search history.

(56) References Cited

U.S. PATENT DOCUMENTS

| | | | |
|---|---|---|---|
| 4,737,360 A | | 4/1988 | Allen et al. |
| RE33,107 E | | 11/1989 | Dikstein et al. |
| 5,350,774 A | | 9/1994 | Palou |
| 5,578,312 A | * | 11/1996 | Parrinello .................... 424/401 |
| 5,824,323 A | | 10/1998 | Fishman |
| 5,916,573 A | | 6/1999 | Spiers et al. |
| 6,024,943 A | * | 2/2000 | Ness et al. ..................... 424/59 |
| 6,193,987 B1 | | 2/2001 | Harbeck |
| 6,228,387 B1 | | 5/2001 | Borod |
| 6,479,043 B1 | | 11/2002 | Tietjen et al. |
| 6,572,868 B1 | | 6/2003 | Cope |
| 6,576,269 B1 | | 6/2003 | Korneyev |
| 6,676,951 B1 | * | 1/2004 | Champ et al. .............. 424/400 |

FOREIGN PATENT DOCUMENTS

| | | |
|---|---|---|
| FR | 2806906 | 5/2001 |
| WO | WO 01/37792 A2 | 5/2001 |

OTHER PUBLICATIONS

*The Super Antioxidants*, J.F. Balch, M.D., M. Evans and Company, Inc., New York, 1998, p. 116.
*The Healing Power of Vitamins, Minerals and Herbs*, Readers Digest Association, Inc., Pleasantville, NY, 1999, pp. 110-111, 192-193, 258-259, 364-365,372-373.
"Vitamin E Oil (D-Alpha Tocopheryl Acetate 550 IU per ml) 32 oz: K", publiished at http:www.shamanshop.net/store/proddetail.cfm/ItemID/12102.0/CategoryID/4500.0/Su . . . on Oct. 20, 2003.

* cited by examiner

*Primary Examiner*—Christopher R. Tate
(74) *Attorney, Agent, or Firm*—Richard C. Litman

(57) ABSTRACT

The skin formulation is a non-alcoholic composition for treating and alleviating skin disorders, including dermatitis, rough skin, cracking, itching and psoriasis. The formulation includes only natural ingredients. All oils in the formulation are unadulterated or minimally processed and do not result in irritation to the skin or other harmful side effects. The compositions can be formulated as a lotion, lotion bar, or a soap.

9 Claims, No Drawings

SKIN FORMULATION

BACKGROUND OF THE INVENTION

1. Field of the Invention

The present invention relates to a composition for treating skin disorders, and particularly to a non-alcoholic composition of natural ingredients for treating dermatitis, severe dry skin, and psoriasis.

2. Description of the Related Art

Skin disorders, as the term is used herein, encompasses numerous skin conditions ranging in severity from severe dermatitis, severe dry skin, psoriasis, etc., to less severe conditions, such as lack of adequate skin firmness, dermal hydration or sebum secretion, etc., which are nonetheless unsightly and may cause physical discomfort.

Until now, the treatment of skin disorders has been largely based on non-specific drugs, and only limited success has been achieved. Dermatitis, for example, which may be accompanied by severe scaling, fissures, edema, oozing, erosion, itching and thickening of the skin, commonly has been treated with corticosteroids. Such compounds provide symptomatic relief for some patients. Steroids, however, are known to produce many local and systemic side effects, and their long term use may not be desirable.

Similarly Vitamin D is therapeutically effective in treating certain skin disorders, but only in dosages which are associated with undesirable side effects. Vitamin D at the dose ranges used in currently marketed topical preparations is not therapeutically effective against contact dermatitis.

Other formulations for treating skin disorders have either been ineffective or have caused significant irritation to the skin.

Several formulations have been proposed to overcome the disadvantages of the prior art, both for treating skin disorders, and for use in cosmetics in order to prevent skin irritation and clear blemishes.

U.S. Pat. No. 6,572,868, issued Jun. 3, 2003 to Sandra E. Cope, discloses a restructuring complex for cosmetic compositions. The composition comprises safe and effective amounts of carrageenans, borage seed oil, squalane, ceramide 3, ceramide 6, red algae extract, dipalmitoyl hydroxproline, and oleuropein.

U.S. Pat. No. 6,193,987, issued Feb. 27, 2001 to M. H. Harbeck, discloses a lubricating composition for the hands and skin. The composition has as its constituents a mixture of organic safflower oil, flaxseed oil, tincture of benzoin, and organic beeswax.

U.S. Pat. No. 6,479,043, issued Nov. 12, 2002 to Tietjen et al., discloses a depilatory composition. The composition includes emollients, skin conditioners, buffering agents, viscosity increasing agents, emulsion stabilizers, pH adjusters, chelating agents, fragrance, color, lubricants, propellants, or biological agents.

Other related patents include U.S. Pat. No. Re. 33,107, issued Nov. 7, 1989 to Dickstein et al. (compositions containing 1 α-hydroxycholecalciferol for topical treatment of skin disorders and methods employing same); U.S. Pat. No. 4,737,360, issued Apr. 12, 1988 to Allen et al. (skin care compositions comprising a pollen extract and non-animal and non-mineral oils); U.S. Pat. No. 5,350,774, issued Sep. 27, 1994 to C. Palou (therapeutic preparation for topical application to the skin); U.S. Pat. No. 5,824,323, issued Oct. 20, 1998 to Y. Fishman (skin lotion composition and softgel filled therewith and methods for making and using same); U.S. Pat. No. 5,916,573, issued Jun. 29, 1999 to Spiers et al. (topical treatment of the skin with a grape seed oil composition); U.S. Pat. No. 6,576,269, issued Jun. 10, 2003 to Korneyev (treating open skin lesions using extract of sea buckthorn); WO 01/37792, published May 31, 2001 (cosmetic skin care composition); and French Patent No. 2,806, 906, published Oct. 5, 2001 (composition for use on the skin surrounding the eyes and mouth).

Various topical formulations and oral regimens of vitamins and herbs have been proposed for the treatment of skin conditions. U.S. Pat. No. 6,228,387, issued May 8, 2001 to M. Borod, describes a first composition for topical application and a second composition for oral administration for the treatment of hemorrhoids. The topical composition includes several herbs and vitamins, including grape seed extract and vitamin E, and in one embodiment, a few drops of Essential Oil of Chamomile.

Vitamin E occurs naturally as a mixture of tocopherols, the most active being α-tocopherol. Vitamin E occurs naturally in wheat germ, vegetable oils, and nuts, particularly almonds. The international unit of vitamin E is equal to one milligram of dl-α-tocopheryl acetate. According to a web page published on the Shaman Shop web site on Oct. 20, 2003, used externally, vitamin E is healing to the skin, being used for protection from sun damage, reducing facial lines and wrinkles, and improving skin smoothness, being used as an additive to massage oils and face creams.

Grape seed extract is reported to act synergistically with vitamins A and E to enhance their antioxidant effectiveness, according to J. F. Balch, M.D., *The Super Antioxidants*, Evans and Company, Inc., New York (1998), at page 116.

*The Healing Power of Vitamins, Minerals and Herbs*, published by the Reader's Digest Association, Inc. in 1999, reports, at pages 110–111, that evening primrose oil, vitamins A and E, grape seed extract, and topical creams containing chamomile have been found useful for eczema or dermatitis. The same reference reports vitamin A and grape seed extract also useful for psoriasis at pages 192–193. Topical application of chamomile oil mixed with almond oil is recommended at page 258–259 of the same reference for relief of sunburn. Vitamin A has been used to treat eczema, psoriasis, and other skin conditions, ibid. at pp. 372–373. Beta-carotene, or provitamin A, is a substance readily converted into Vitamin A upon absorption into the body, and is found naturally in carrots, apricots, mangoes, and other yellow, orange and red fruits. Finally, external application of tea tree oil has been found effective as an antifungal agent, ibid. pp. 364–365.

None of the above inventions and patents, taken either singly or in combination, is seen to describe the instant invention as claimed. In particular, none of the above patents or publications has described a composition combining all of the naturally occurring ingredients of the present skin formulation for topical application, and none have proven as effective as the present skin formulation for treatment of dermatitis and psoriasis. Thus, a skin formulation solving the aforementioned problems is desired.

SUMMARY OF THE INVENTION

The skin formulation of the present invention is a non-alcoholic composition for treating and alleviating skin disorders, including dermatitis, rough skin, cracking, itching and psoriasis. The formulation includes only natural ingredients. All oils in the formulation are unadulterated or minimally processed and do not result in irritation to the skin or other harmful side effects. The compositions can be formulated as a lotion, lotion bar, or soap. The lotion and lotion bar include, in one embodiment, shea butter, mango butter, beeswax, chamomile, carrot seed oil, rosemary oil, cedar wood oil, rosewood oil, rosehips oil, grapefruit seed extract, and sweet orange oil. The soap is made, in one embodiment, from olive oil, coconut oil, palm oil, sodium hydroxide, shea butter, rosehips oil and a mixture of oils, including equal parts of chamomile (German, blue, or Roman), carrot seed oil, rosemary oil, Virginia cedar wood oil, and rosewood oil.

Accordingly, it is a principal object of the invention to provide a skin formulation for treating skin disorders.

It is another object of the invention to provide a skin formulation which includes only ingredients that are naturally occurring.

It is a further object of the invention to provide a skin formulation which is alcohol free.

Still another object of the invention is to provide a skin formulation which does not cause adverse side affects.

It is an object of the invention to provide improved elements and arrangements thereof for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention relates to a formulation for treating and alleviating skin disorders including, but not limited to, dermatitis, rough skin, cracking, itching and psoriasis.

In one embodiment, the formulation can be prepared as a lotion or as a lotion bar and includes generally (1) about 40%–60% shea butter (also known as karite butter); 2) about 10%–30% mango butter; 3) about 5%–20% sweet, unadulterated almond oil; 4) about 5%–15% unadulterated apricot oil or refined apricot kernel oil; 5) about 3%–15% unadulterated or refined jojoba oil; 6) about 3%–15% unadulterated or refined grape seed oil; 7) about 2%–15% unadulterated evening primrose oil; 8) about 0.5%–8% Vitamin E oil; 9) about 10%–20% pure or bleached beeswax; 10) about 0.3%–5% German chamomile (pure essential oil only); 11) about 0.5%–5% carrot seed oil (pure essential oil only); 12) about 0.3%–5% pure essential rosemary oil; 13) about 0.3%–5% Virginia cedar wood, atlas, or any essential cedar wood oil; 14) about 0.3%–5% rosewood oil or other essential oil possessing the same therapeutic qualities; 15) about 0.31–5% rosehips oil; 16) about 0.2%–5% grapefruit seed extract; 17) about 0.5%–5% sweet orange oil and; 18) about 0–40% purified, distilled, or sterile water. The shea butter is preferably pure or minimally processed without benzene, propyl alcohol, or petroleum distillates. Additionally, about 0.001%–2% *Lippia javanica* and/or about 0.8% Tea Tree oil may optionally be added to the mixture.

In a more preferred embodiment, the lotion formulation includes a) about 907 grams (32 oz.) shea butter (pure or minimally processed); b) about 453 grams (16 oz.) mango butter; c) about 226 grams (8 oz.) sweet almond oil; d) about 226 grams (8 oz.) apricot kernel oil; e) about 170 grams (6 oz.) jojoba oil; f) about 141 grams (5 oz.) grape seed oil; g) about 85 grams primrose oil; h) about 28 grams (1 oz.) Vitamin E oil; i) about 680 grams (3 cups) pure beeswax alone or with about 99 grams (5 tablespoons) an emulsifier; j) about 56.69 grams (4 tablespoons) of German chamomile; k) about 42.52 grams (3 tablespoons) carrot seed oil; l) about 42.52 grams (3 tablespoons) rosemary extract essential oil; m) about 28.34 grams (2 tablespoons) atlas, Virginia, or any pure essential cedar wood oils; n) about 42.52 grams (3 tablespoons) rosewood essential oil; o) about 56.69 grams (4 tablespoons) rosehips oil; p) about 7.08 grams (½ tablespoon) grapefruit seed extract; and q) about 28.34 grams (2 tablespoons) essential tangerine oil, sweet orange oil, or mandarin orange oil. About 226–340 grams (8–12 oz.) sterile water may also be added.

For preparing the lotion from the ingredients described above, ingredients (c)-(g) and one-half of the beeswax are heated to 100° F. until melted. As soon as the oils are melted, they can be blended with water if desired. Ingredients (h) and (j)-(q) are then poured into the mixture. Preferably, the mixture is blended for five minutes and then poured into a warm, clean container. The container is sealed and stored overnight. After twenty-four hours, the mango butter and the remaining beeswax are melted together. The mixture which had been set aside overnight is then emptied into a blending container, and then slowly, preferably at a rate of one ounce per five seconds, the melted mango and pure beeswax are poured into the container. The shea butter is then added into the mixture. The entire mixture is then blended for approximately five minutes and then allowed to aerate. The mixture is then poured into clean containers, covered with breathable, sterile cloth, and set aside for forty-eight hours. In all instances where heating or melting of the ingredients is required, a double boiler, stainless steel pot is preferably used.

In a preferred embodiment for the lotion bar, the formulation includes a) about 42.52 grams shea butter (3 tablespoons); b) 42.52 grams mango butter (3 tablespoons); c) about 56.69 grams (¼ cup) almond and apricot kernel oil; d) about 42.52 grams (3 tablespoons) evening primrose oil; e) about 42.52 grams (3 tablespoons) jojoba oil; f) about 42.52 grams (3 tablespoons) grape seed oil; g) about 14.17 grams (1 tablespoon) rosehips oil; h) about 14.17 grams (1 tablespoon) Vitamin E oil; i) about 680 grams (3 cups) pure beeswax; j) about 14.17 grams (1 tablespoon) essential carrot seed oil; k) about 14.17 grams (1 tablespoon) rosewood essential oil; l) about 14.17 grams (1 tablespoon) atlas, Virginia, or any pure essential cedar wood oils; m) about 14.17 grams (1 tablespoon) rosemary extract oil; n) about 28.34 grams (2 tablespoons) of German chamomile oil; o) about 3.54 grams (¼ tablespoon) grapefruit seed extract; and p) about 3.54 grams (¼ tablespoon) essential tangerine oil, sweet orange oil, mandarin orange oil, or any essential orange oil.

For preparing the lotion bar, the beeswax is melted with ingredients (a)-(f). Once melted, the mixture is allowed to cool until partially thickened. The remaining ingredients, (g), (h), and (j)-(p) are combined into the mixture (preferably by hand). The mixture is then placed in rectangular molds and allowed to harden. After the mixture has hardened, it is removed from the molds, wrapped, and packaged, if desired.

In yet another embodiment, the formulation is prepared as a soap. The soap is prepared from 1) about 10%–50% by weight of almond oil or olive oil; 2) about 10%–50% by weight of coconut oil; 3) about 10%–50% by weight of palm oil; 4) about 1–10% by weight of sodium hydroxide; 5) about 1%–15% shea butter; 6) about 0.2%–10% of a mixture including equal parts of chamomile (German, blue, or Roman), carrot seed oil, rosemary oil, Virginia cedar wood, rosewood oil, rosehips oil, grapefruit seed oil, and essential sweet orange.

In a preferred embodiment for the soap, the formulation is made from a) about 272.15 grams (9.6 oz.) olive oil; b) about 181.43 grams (6.4 oz.) shea butter; c) about 56.69 grams (2 oz.) mango butter; d) about 272.15 grams (9.6 oz.) coconut oil; e) about 181.43 (6.4 oz.) grams palm oil; f) about 340.19 grams (12 oz.) purified or sterile water; g) about 127.57 grams (4.5 oz.) sodium hydroxide; h) about 3.96 grams (0.14 oz.) essential oils including equal parts of German chamomile, carrot seed oil, rosemary oil, Virginia cedar wood, and rosewood essential oils; i) about 0.83 grams (10 gtts., or drops) Vitamin E oil; j) about 0.83 grams (10 gtts., or drops) rosehips oil k) about 85.04 grams oatmeal (3 oz.); and 1) about 85.04 grams (3 oz.) finely ground apricot kernel.

For preparing the soap from the ingredients described above, ingredients (f) and (g) are mixed together, preferably in a glass container. The mixture is then allowed to cool to about 110 degrees Fahrenheit. Ingredients (a) thru (e) are mixed together in a separate, heated container (preferably stainless steel) until melted. This mixture is also allowed to cool to about 110 degrees Fahrenheit. When both mixtures have cooled to 110 degrees Fahrenheit, they are mixed together until they have reached "trace". Trace is reached when the mixture has thickened somewhat, similar to the consistency of pudding after it is cooked. Ingredients (h), (i), and (j) are then added to the mixture. Ingredients (k) and (1) are added to the mixture last and mixed for about thirty seconds. The ingredients are then placed in a mold and set aside for about twenty-eight to forty-eight hours.

The ingredients disclosed for the above lotion, lotion bar, and soap formulations may be substituted for other ingredients as provided herein. The shea butter may be replaced by mango or cocoa butters, jojoba, or coconut oil. The mango butter may be replaced with shea butter, coconut, jojoba, grape seed, or avocado oils. The almond oil may be replaced with mango butter, karite butter, apricot kernel oil, jojoba oil, coconut oil, hemp seed oil, borage oil, neem tree oil, almond butter, olive oil, lard, vegetable oil, coconut oil, palm kernel, or palm oil. Apricot kernel oil, shea butter, jojoba oil, coconut oil, hemp seed oil, borage oil, sweet almond oil, or babasu oil may be used to replace the apricot oil. Coconut oil, apricot kernel oil, shea butter, mango butter, hemp seed oil, borage oil, avocado oil, or evening primrose oil may be substituted for the jojoba oil. The grape seed oil may be replaced with almond oil, hemp seed oil, borage oil, apricot oil, avocado oil or shea butter. The evening primrose oil may be replaced by Vitamin E oil, hemp seed oil, borage oil, grape seed oil, or avocado oil. Rose hips oil may be substituted for Vitamin E oil. Roman chamomile, blue chamomile, or any other chamomile containing azulene may be substituted for the German chamomile. Rosemary or Vitamin E may be used in place of the rosehips oil. Bitter orange oil, tangerine oil, or mandarin orange oil may be substituted for the sweet orange oil. All oils in the formulation are unadulterated or minimally processed.

The emulsifier used in the present invention is preferably any vegetable based emulsifying wax. A vegetable based emulsifying wax from Rainbow Meadow, Inc. is most preferable. The vegetable based emulsifier may also be substituted for pure beeswax.

Vitamin E oil, as used herein, may include a mixture of tocopherols, but preferably is exclusively or primarily α-tocopherol. More preferably, the oil contains d-α-tocopherol, i.e., Vitamin E oil derived from natural sources, rather than synthetic Vitamin E.

The lotion, lotion bar, and the soap may be used individually for providing relief to the skin. For maximum effectiveness, however, the lotion, the lotion bar, and the soap are all applied to the affected area of the skin. The lotion is applied to the skin after the skin is washed with the soap. The lotion bar is then applied over the lotion. The lotion bar covers the lotion layer and helps the formulation to penetrate into the skin. Preferably, the soap is used once a day and the lotion and lotion bar are used 2–3 times a day. If desired, the lotion bar may be rubbed on the skin throughout the day, as needed, to minimize itching.

The ingredients for producing the present formulations are readily available and can be inexpensively mixed on a commercial scale in any suitable manner known in the art. The preferred methodologies for making the lotion, lotion bar, and soap set forth above are only exemplary.

For a more complete understanding of the present improved composition, reference is made to the following examples. The following examples are illustrative of the present improved composition and are not intended in any way as a limitation upon the scope thereof.

EXAMPLE 1

The lotion, lotion bar, and soap of the present invention were used to treat the scalp of a woman suffering from flaky, irritated skin. The soap was used once a day and the lotion and lotion bar were used 2–3 times a day. Within forty-eight hours of use, the flaking stopped and the red irritation was significantly lessened.

EXAMPLE 2

A female user suffering from psoriasis used the lotion, lotion bar, and soap of the present invention to treat her skin. The soap was used once a day and the lotion and lotion bar were used 2–3 times a day. After two months of regular use, the psoriasis lesions improved significantly, swelling and scales on her skin diminished, and her skin became more flexible. She had previously tried over-the-counter creams, lotions and soaps, as well as prescription steroids, coal tars and bath salts, with no success.

EXAMPLE 3

A female user suffering from dermatitis used the lotion, lotion bar, and soap of the present invention to treat dry, cracked, bleeding palms. After ten days of regular use, the cracks, bleeding, and white patches were gone. After one month, underlying tissues became soft and no longer hard to the touch. The lotion, lotion bar, and soap of the present invention were used in the morning and before going to bed.

EXAMPLE 4

A male user suffering from psoriasis used the lotion, lotion bar, and soap of the present invention for three weeks. After three weeks of use, white skin began to develop. The scaling, which was previously visible on the user's skin, diminished, and itching was significantly decreased. The soap, lotion bar, and lotion were used twice a day every day.

EXAMPLE 5

A male user suffering from psoriasis used the lotion, lotion bar, and soap of the present invention to treat irritated skin. The user's skin had developed scaly raised areas and large red spots. The user treated the skin once every 4–5 days. After three weeks, the red spots and bumps started to diminish, the flakiness stopped, and the skin became smoother.

EXAMPLE 6

A male user had psoriasis for twenty years. Upon treating the irritated skin with the lotion, lotion bar, and soap of the present invention, for one day, the itching stopped. A great reduction in scales and raised areas was noted after less than one week of use.

It is to be understood that the present invention is not limited to the embodiments described above, but encompasses any and all embodiments within the scope of the following claims.

I claim:

1. A skin formulation, comprising:
   a) about 40%–60% by volume shea butter;
   b) about 10%–30% by volume mango butter;
   c) about 10%–20% by volume beeswax;
   d) about 5%–20% by volume of almond oil;
   e) about 5%–15% by volume of apricot oil;
   f) about 3%–15% by volume of jojoba oil;
   g) about 3%–15% by volume of grape seed oil;
   h) about 2%–15% by volume of primrose oil;
   i) about 0.5%–8% by volume of Vitamin E oil;
   j) about 0.3%–5% chamomile
   k) about 0.5%–5% by volume carrot seed oil;
   l) about 0.3%–5% by volume of rosemary oil;
   m) about 0.3%–5% by volume cedar wood oil;
   n) about 0.3%–5% by volume rosewood oil;
   o) about 0.3%–5% by volume rosehips oil;
   p) about 0.3%–5% by volume grapefruit seed oil; and
   q) about 0.5%–5% by volume of an oil selected from the group consisting of sweet orange oil, bitter orange oil, tangerine oil, and mandarin orange oil.

2. The skin formulation according to claim 1, wherein said chamomile is selected from the group consisting of German chamomile, blue chamomile, and Roman chamomile.

3. The skin formulation according to claim 1, further comprising about 5%–20% by volume of an ingredient selected from the group consisting of karite butter, coconut oil, hemp seed oil, borage oil, neem tree oil, olive oil, lard, vegetable oil, coconut oil, palm kernel, palm oil, avocado oil, and babasu oil.

4. The skin formulation according to claim 1, further comprising about 0.001%–2% by volume of Lippia javanica.

5. The skin formulation according to claim 1, further comprising about 0–40% by volume water.

6. The skin formulation according to claim 1, wherein the formulation is formed as a lotion.

7. The skin formulation according to claim 1, wherein the formulation is formed as a lotion bar.

8. A skin formulation comprising:
   a) about 10%–50% by weight of an oil selected from the group consisting of almond oil and olive oil;
   b) about 10%–50% by weight of coconut oil;
   c) about 10%–50% by weight of palm oil;
   d) about 1%–15% by weight of shea butter; and
   e) about 0.2%–10% of a mixture including equal parts of chamomile, carrot seed oil, rosemary oil, Virginia cedar wood, rosewood oil, rosehips oil, grapefruit seed oil, and essential sweet orange.

9. The skin formulation according to claim 8, wherein the formulation is formed into a soap.

* * * * *